(12) United States Patent
Takemoto et al.

(10) Patent No.: US 11,672,516 B2
(45) Date of Patent: Jun. 13, 2023

(54) CONTROL APPARATUS, CONTROL METHOD, AND CONTROL SYSTEM

(71) Applicant: SONY CORPORATION, Tokyo (JP)

(72) Inventors: Masaya Takemoto, Kanagawa (JP); Yuki Sugie, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 884 days.

(21) Appl. No.: 16/494,039

(22) PCT Filed: Feb. 21, 2018

(86) PCT No.: PCT/JP2018/006226
§ 371 (c)(1),
(2) Date: Sep. 13, 2019

(87) PCT Pub. No.: WO2018/173606
PCT Pub. Date: Sep. 27, 2018

(65) Prior Publication Data
US 2020/0022687 A1    Jan. 23, 2020

(30) Foreign Application Priority Data
Mar. 22, 2017  (JP) .............................. JP2017-056090

(51) Int. Cl.
*A61B 17/00*  (2006.01)
*G06T 7/00*  (2017.01)

(52) U.S. Cl.
CPC ............ *A61B 17/00* (2013.01); *G06T 7/0012* (2013.01); *A61B 2017/00022* (2013.01); *G06T 2207/10068* (2013.01)

(58) Field of Classification Search
CPC .......... A61B 17/00; A61B 2017/00022; G06T 7/0012; G06T 2207/10068
USPC .............................................. 606/1
See application file for complete search history.

(56) References Cited

FOREIGN PATENT DOCUMENTS

| JP | 11-309156 A | 11/1999 |
|---|---|---|
| JP | 2013-039224 A | 2/2013 |
| JP | 2016-158886 A | 9/2016 |

*Primary Examiner* — Aaron F Roane
(74) *Attorney, Agent, or Firm* — Chip Law Group

(57) ABSTRACT

[Object] To effectively eliminate an effect of smoke that is generated by cauterization of a tissue. [Solving Means] Provided is a control apparatus including a control unit configured to control smoke removal processing on an image of a living body taken during surgery and actual smoke evacuation of smoke in the living body, in which the control unit allows execution of at least the smoke removal processing on the basis of a fact that the smoke has been detected. Also provided is a control system including: an endoscope configured to take an image of a living body during surgery; a control apparatus configured to control smoke removal processing on the image of the living body and actual smoke evacuation of smoke in the living body; and a smoke evacuation apparatus configured to execute the actual smoke evacuation of the smoke on a basis of control by the control apparatus, in which the control apparatus executes at least the smoke removal processing on a basis of a fact that the smoke has been detected.

19 Claims, 11 Drawing Sheets

CONTROL APPARATUS, CONTROL METHOD, AND CONTROL SYSTEM

CROSS REFERENCE TO RELATED APPLICATIONS

This application is a U.S. National Phase of International Patent Application No. PCT/JP2018/006226 filed on Feb. 21, 2018, which claims priority benefit of Japanese Patent Application No. JP 2017-056090 filed in the Japan Patent Office on Mar. 22, 2017. Each of the above-referenced applications is hereby incorporated herein by reference in its entirety.

TECHNICAL FIELD

The present disclosure relates to a control apparatus, a control method, a control system, and a program.

BACKGROUND ART

In recent years, in medical sites, endoscopic surgery using endoscopes has widely been carried out. Further, various apparatus for use in endoscopic surgery have been developed. For example, PTL 1 discloses a smoke evacuation apparatus configured to evacuate smoke inside a body cavity in response to a cauterization processing signal from an electrocauterizer.

CITATION LIST

Patent Literature

[PTL 1]
Japanese Patent Laid-open No. Hei 11-309156

SUMMARY

Technical Problems

However, in general, an amount of smoke to be generated varies depending on tissues to be cauterized, and hence the smoke evacuation apparatus described in PTL 1, which evacuates smoke on the basis of cauterization processing signals from the electrocauterizer, possibly evacuates smoke too much or too little. Further, a period of time from when the electrocauterizer starts to operate to when a surgeon brings the electrocauterizer into contact with a tissue is not always the same, and it is thus assumed that the smoke evacuation apparatus described in PTL 1 has a time lag between generation of smoke and evacuation.

In view of this, the present disclosure proposes a control apparatus, a control method, a control system, and a program that are novel and enhanced and are capable of effectively eliminating an effect of smoke that is generated by cauterization of a tissue.

Solution to Problems

According to the present disclosure, there is provided a control apparatus including a control unit configured to control smoke removal processing on an image of a living body taken during surgery and actual smoke evacuation of smoke in the living body, in which the control unit allows execution of at least the smoke removal processing on the basis of a fact that the smoke has been detected.

Further, according to the present disclosure, there is provided a control method including controlling, by a processor, smoke removal processing on an image of a living body taken during surgery and actual smoke evacuation of smoke in the living body, in which the controlling includes allowing execution of at least the smoke removal processing on the basis of a fact that the smoke has been detected.

Further, according to the present disclosure, there is provided a control system including: an endoscope configured to take an image of a living body during surgery; a control apparatus configured to control smoke removal processing on the image of the living body and actual smoke evacuation of smoke in the living body; and a smoke evacuation apparatus configured to execute the actual smoke evacuation of the smoke on the basis of control by the control apparatus, in which the control apparatus executes at least the smoke removal processing on the basis of a fact that the smoke has been detected.

Further, according to the present disclosure, there is provided a program for causing a computer to function as a control apparatus, the control apparatus including a control unit configured to control smoke removal processing on an image of a living body taken during surgery and actual smoke evacuation of smoke in the living body, in which the control unit allows execution of at least the smoke removal processing on the basis of a fact that the smoke has been detected.

Advantageous Effect of Invention

As described above, according to the present disclosure, the effect of smoke that is generated by cauterization of a tissue can be effectively eliminated.

Note that the above-mentioned effect is not necessarily limited, and any effect described herein or other effects that may be grasped from the present specification may be provided in addition to the above-mentioned effect or instead of the above-mentioned effect.

BRIEF DESCRIPTION OF DRAWINGS

FIG. 1 is a diagram illustrating an example of a state of surgery to which an operating room system using technical ideas according to the present disclosure is applied.

FIG. 2 is a diagram illustrating an example of a system configuration according to a first embodiment of the present disclosure.

FIG. 3 is a flow chart illustrating a flow of smoke detection and smoke amount calculation by a smoke detection unit according to the first embodiment.

FIG. 4 is a diagram illustrating a relationship between smoke removal processing and actual smoke evacuation that are controlled by a control unit according to the first embodiment, and an amount of smoke according to the present embodiment.

FIG. 5 is a flow chart illustrating a flow of basic operation of a control apparatus according to the first embodiment.

FIG. 6 is a flow chart illustrating a flow of actual smoke evacuation control based on smoke detection after the smoke removal processing by the control apparatus according to the first embodiment.

FIG. 7 is the first embodiment.

FIG. 8 is a diagram illustrating an example of a system configuration according to a second embodiment of the present disclosure.

FIG. 9 is a diagram illustrating an example of a system configuration according to a third embodiment of the present disclosure.

FIG. 10 is a diagram illustrating an example of a system configuration according to a fourth embodiment of the present disclosure.

FIG. 11 is a diagram illustrating an example of a hardware configuration of a control system according to one embodiment of the present disclosure.

DESCRIPTION OF EMBODIMENTS

Figure 1:
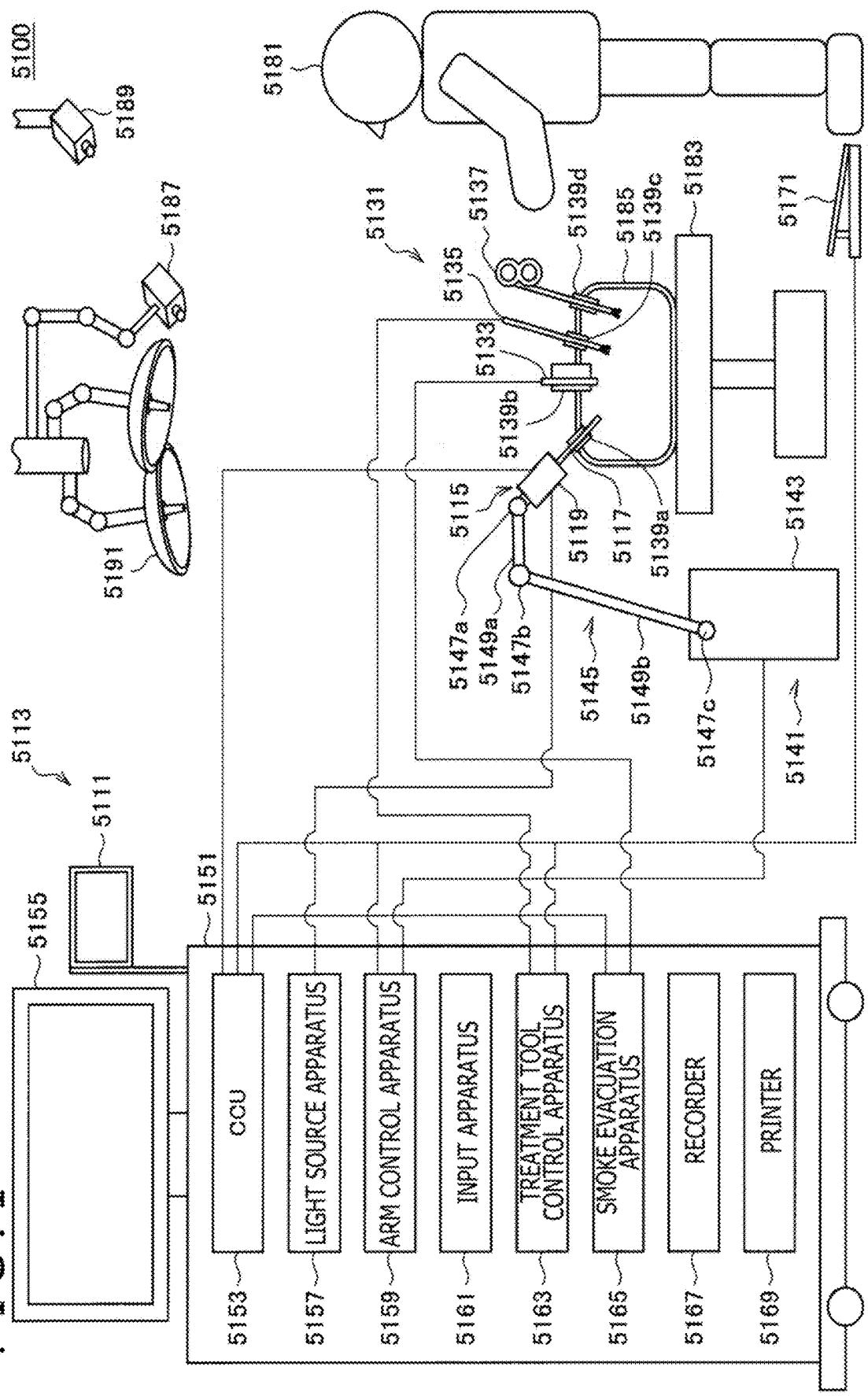
FIG. 1

Now, preferred embodiments of the present disclosure are described in detail with reference to the attached drawings. Note that, in the present specification and the drawings, components having substantially the same functional configurations are denoted by the same reference symbols, so that overlapped description is omitted.

Note that the following items are described in order.
1. Background
2. Application Example
3. First Embodiment
3.1. System Configuration
3.2. Flow of Operation of Control Apparatus 20
4. Second Embodiment
4.1. System Configuration Example
5. Third Embodiment
5.1. System Configuration Example
6. Fourth Embodiment
6.1. System Configuration Example
7. Hardware Configuration Example
8. Conclusion

1. BACKGROUND

The background that leads to the present technical ideas is first described. As described above, in recent years, endoscopic surgery using endoscopes has widely been carried out. In endoscopic surgery, an image of a living body of an object to be observed (patient) is taken with an endoscope inserted into the object to be observed, so that a surgeon can perform an inspection or a medical procedure while observing the image of the living body.

Meanwhile, in endoscopic surgery, a space inside an object to be observed is filled with smoke generated by an energy treatment tool, such as an electrocauterizer, cauterizing a tissue, with the result that the definition of a taken image of a living body is affected in some cases. This means that smoke appears in the image of the living body to affect the surgical field, so that a surgeon cannot observe the tissue efficiently.

Endoscopic surgery thus requires a mechanism for appropriately discharging smoke generated inside an object to be observed. As the mechanism for smoke evacuation, manually opening or closing a cylindrical hole opening instrument, which is called "trocar," by a surgeon or using a smoke evacuation apparatus, such as the one disclosed in PTL 1, is assumed. With these mechanisms, however, it is sometimes difficult to adjust a smoke evacuation amount to a value suitable for situations. It is thus assumed that the apparatus as described above causes a reduction in observation efficiency due to insufficient smoke evacuation, an increase in pneumoperitoneum gas cost due to excessive smoke evacuation, or effects on an object to be observed due to hemodynamics changes.

The present technical ideas have been conceived in the light of the above-mentioned points, and make it possible to appropriately eliminate the effect of smoke depending on situations. In order to realize this, a control apparatus, a control method, a control system, and a program according to one embodiment of the present disclosure have a feature of controlling, on the basis of detected smoke, both of smoke removal processing on a taken image of a living bogy and actual smoke evacuation of smoke in the living body. With the above-mentioned feature according to the present technical ideas, insufficient smoke evacuation or excessive smoke evacuation are not caused, and the effect of smoke can therefore be effectively eliminated.

2. APPLICATION EXAMPLE

Next, an application example of the technical ideas that is common between the embodiments of the present disclosure is described. FIG. 1 is a diagram illustrating an example of the state of surgery to which an operating room system 5100 using the technical ideas according to the present disclosure is applied. A ceiling camera 5187 and an operating theater camera 5189 are provided on the ceiling of an operating room, and are capable of capturing an image of an area around the hands of a surgeon (doctor) 5181 treating an affected area of a patient 5185 on a patient bed 5183 and an image of the whole operating room. The ceiling camera 5187 and the operating theater camera 5189 may have a magnification adjustment function, a focal length adjustment function, and an image capturing direction adjustment function, for example. A lighting 5191 is provided on the ceiling of the operating room and illuminates at least the area around the hands of the surgeon 5181. The irradiation light amount, wavelength (color) of irradiation light, and light irradiation direction of the lighting 5191 may be appropriately adjustable, for example.

An endoscopic surgery system 5113, the patient bed 5183, the ceiling camera 5187, the operating theater camera 5189, and the lighting 5191 are connected to each other in a cooperated manner through an audiovisual controller and an operating room control apparatus (not illustrated). In the operating room, a centralized operation panel 5111 is provided, and the user can appropriately operate these apparatus in the operating room through the centralized operation panel 5111.

Now, the configuration of the endoscopic surgery system 5113 is described in detail. As illustrated in FIG. 1, the endoscopic surgery system 5113 includes an endoscope 5115, other surgical instruments 5131, a support arm apparatus 5141 configured to support the endoscope 5115, and a cart 5151 having mounted thereon various apparatus for endoscopic surgery.

In endoscopic surgery, instead of cutting the abdominal wall to perform laparotomy, a plurality of trocars 5139a to 5139d, which are cylindrical hole opening instruments, are inserted into the abdominal wall. Then, through the trocars 5139a to 5139d, a lens barrel 5117 of the endoscope 5115 and the surgical instruments 5131 are inserted into the body cavity of the patient 5185. In the example illustrated in FIG. 1, as the surgical instruments 5131, a tube 5133, an energy treatment tool 5135, and forceps 5137 are inserted into the body cavity of the patient 5185. Here, the tube 5133 may evacuate smoke generated inside the body cavity to outside the body cavity. Meanwhile, the tube 5133 may further function to inject gas into the body cavity, thereby inflating the body cavity. Further, the energy treatment tool 5135 is a treatment tool for, for example, incising or peeling a tissue or sealing a blood vessel with high-frequency current or ultrasonic vibration. Note that the surgical instruments 5131 illustrated in FIG. 1 are merely examples, and as the surgical instruments 5131, various surgical instruments that are generally used in endoscopic surgery, such as tweezers and a retractor, may be used.

An image of a surgical region inside the body cavity of the patient 5185 captured by the endoscope 5115 is displayed on a display apparatus 5155. The surgeon 5181 performs medical treatment, such as resection of an affected area, using the energy treatment tool 5135 or the forceps 5137 while looking at the image of the surgical region displayed on the display apparatus 5155 in real time. Note that, although not illustrated, the tube 5133, the energy treatment tool 5135, and the forceps 5137 are supported by the surgeon 5181 or an assistant, for example, during surgery.

(Support Arm Apparatus)

The support arm apparatus 5141 includes an arm portion 5145 that extends from a base portion 5143. In the example illustrated in FIG. 1, the arm portion 5145 includes joint portions 5147*a*, 5147*b*, and 5147*c*, and links 5149*a* and 5149*b*, and is driven under control by an arm control apparatus 5159. The arm portion 5145 supports the endoscope 5115 to control the position and posture thereof. With this, the endoscope 5115 may be stably fixed at a position.

(Endoscope)

The endoscope 5115 includes the lens barrel 5117 having a region of a predetermined length from the distal end thereof that is inserted into the body cavity of the patient 5185, and a camera head 5119 that is connected to the proximal end of the lens barrel 5117. In the example illustrated in FIG. 1, the endoscope 5115 is a so-called rigid endoscope and includes the lens barrel 5117 with rigidity, but the endoscope 5115 may be a so-called flexible endoscope including the lens barrel 5117 with flexibility.

The lens barrel 5117 has, at its distal end, an opening portion into which an objective lens is fitted. To the endoscope 5115, a light source apparatus 5157 is connected, and light generated by the light source apparatus 5157 is guided to the distal end of the lens barrel by a light guide that extends inside the lens barrel 5117, to thereby illuminate an object to be observed inside the body cavity of the patient 5185 through the objective lens. Note that the endoscope 5115 may be a forward-viewing endoscope, a forward-oblique viewing endoscope, or a side-viewing endoscope.

The camera head 5119 includes an optical system and an imaging element, and light reflected by an object to be observed (observation light) is concentrated on the imaging element by the optical system. The observation light is subjected to photoelectric conversion by the imaging element, and an electrical signal corresponding to the observation light, that is, an image signal corresponding to the observation image is thus generated. The image signal is transmitted to a camera control unit (CCU) 5153 as RAW data. Note that the camera head 5119 functions to appropriately drive the optical system, to thereby adjust its magnification and focal length.

Note that, to support stereoscopic vision (3D display), for example, the camera head 5119 may include a plurality of imaging elements. In this case, the lens barrel 5117 includes a plurality of relay optical systems for guiding observation light to the plurality of corresponding imaging elements.

(Various Apparatus to be Mounted on Cart)

The CCU 5153 includes, for example, a CPU (Central Processing Unit) or a GPU (Graphics Processing Unit), and controls the operations of the endoscope 5115 and the display apparatus 5155 in a centralized manner. Specifically, the CCU 5153 performs, on an image signal received from the camera head 5119, various kinds of image processing for displaying an image based on the image signal, such as development processing (demosaicing). The CCU 5153 provides the image signal subjected to the image processing to the display apparatus 5155. Further, to the CCU 5153, the above-mentioned audiovisual controller is connected. The CCU 5153 provides the image signal subjected to the image processing also to the audiovisual controller 5107. Further, the CCU 5153 transmits a control signal to the camera head 5119, thereby controlling the drive of the camera head 5119. The control signal may include information associated with imaging conditions, such as a magnification or a focal length. The information associated with the imaging conditions may be input through an input apparatus 5161 or may be input through the centralized operation panel 5111 described above.

The display apparatus 5155 displays, under control by the CCU 5153, an image based on an image signal subjected to the image processing by the CCU 5153. In a case where the endoscope 5115 supports image capturing at high resolution, for example, 4K (horizontal pixel count of 3840×vertical pixel count of 2160) or 8K (horizontal pixel count of 7680×vertical pixel count of 4320) and/or supports 3D display, as the display apparatus 5155, an apparatus supporting high resolution display and/or an apparatus supporting 3D display may be used depending on the respective cases. In the case where the endoscope 5115 supports image capturing at high resolution such as 4K or 8K, an apparatus having a size of 55 inches or more is used as the display apparatus 5155, so that a more immersive experience can be provided. Further, depending on use, a plurality of display apparatus 5155 having different resolutions or sizes may be provided.

The light source apparatus 5157 includes a light source such as an LED (Light Emitting Diode) and supplies irradiation light for image capturing of a surgical region to the endoscope 5115.

The arm control apparatus 5159 includes a processor such as a CPU and operates on the basis of a predetermined program, thereby controlling the drive of the arm portion 5145 of the support arm apparatus 5141 in accordance with a predetermined control method.

The input apparatus 5161 is an input interface for the endoscopic surgery system 5113. The user can input various pieces of information or instructions to the endoscopic surgery system 5113 through the input apparatus 5161. For example, the user inputs various pieces of information associated with surgery, such as physical information of a patient or information regarding surgical a form of surgery, through the input apparatus 5161. Further, for example, the user inputs an instruction to drive the arm portion 5145, an instruction to change the imaging conditions of the endoscope 5115 (kinds of irradiation light, magnification, or focal length, for example), or an instruction to drive the energy treatment tool 5135, through the input apparatus 5161.

The types of the input apparatus 5161 are not limited and the input apparatus 5161 may include various well-known input apparatus. To the input apparatus 5161, for example, a mouse, a keyboard, a touch panel, a switch, a foot switch

5171, and/or a lever may be applied. In a case where a touch panel is used as the input apparatus 5161, the touch panel may be provided on the display surface of the display apparatus 5155.

Alternatively, the input apparatus 5161 may be a device to be mounted on the user, such as a glasses-type wearable device or an HMD (Head Mounted Display), and various kinds of input are made in response to a gesture or line of sight of the user that is detected by any of these devices. Further, the input apparatus 5161 includes a camera capable of detecting a motion of the user, and various kinds of input are made in response to a gesture or line of sight of the user that is detected from a video taken by the camera. In addition, the input apparatus 5161 includes a microphone capable of collecting the voice of the user, and various kinds of input are made by voice through the microphone. With the input apparatus 5161 configured in this way such that various pieces of information can be input in a contactless manner, especially the user who belongs to a clean area (for example, surgeon 5181) can operate equipment belonging to an unclean area in a contactless manner. Further, since the user can operate the equipment without releasing a possessed surgical instrument from his/her hand, the convenience to the user is improved.

A treatment tool control apparatus 5163 controls the drive of the energy treatment tool 5135 for cauterizing or incising a tissue or sealing a blood vessel, for example. A smoke evacuation apparatus 5165 feeds gas into the body cavity of the patient 5185 through the tube 5133 to inflate the body cavity in order to ensure the field of view of the endoscope 5115 and ensure a working space for the surgeon. Further, the smoke evacuation apparatus 5165 functions to evacuate smoke generated inside the body cavity to ensure the field of view of the endoscope 5115. A recorder 5167 is an apparatus capable of recording various pieces of information associated with surgery. A printer 5169 is an apparatus capable of printing various pieces of information associated with surgery in various forms such as a text, an image, or a graph.

Now, a particularly characteristic configuration of the endoscopic surgery system 5113 is described in more detail.

(Support Arm Apparatus)

The support arm apparatus 5141 includes the base portion 5143, which is a base, and the arm portion 5145 that extends from the base portion 5143. In the example illustrated in FIG. 1, the arm portion 5145 includes the plurality of joint portions 5147a, 5147b, and 5147c, and the plurality of links 5149a and 5149b coupled to each other by the joint portion 5147b. In FIG. 1, for simplified illustration, the configuration of the arm portion 5145 is simplified. Actually, the shape, number, and arrangement of the joint portions 5147a to 5147c and the links 5149a and 5149b, the directions of axes of rotation of the joint portions 5147a to 5147c, and so forth may be set appropriately such that the arm portion 5145 has a desired degree of freedom. For example, the arm portion 5145 may preferably be configured so as to have a degree of freedom of 6 degrees of freedom or more. This makes it possible to move the endoscope 5115 freely within the movable range of the arm portion 5145, with the result that the lens barrel 5117 of the endoscope 5115 can be inserted from a desired direction into the body cavity of the patient 5185.

Actuators are provided in the joint portions 5147a to 5147c, and the joint portions 5147a to 5147c are rotatable around predetermined axes of rotation thereof with the actuators being driven. The drive of the actuator may be controlled by the arm control apparatus 5159 to control the rotational angle of each of the joint portions 5147a to 5147c, thereby controlling the drive of the arm portion 5145. With this, the position and posture of the endoscope 5115 may be controlled. Here, the arm control apparatus 5159 can control the drive of the arm portion 5145 by various known control methods such as force control or position control.

When the surgeon 5181 appropriately performs input operation through the input apparatus 5161 (including foot switch 5171), for example, the arm control apparatus 5159 may appropriately control the drive of the arm portion 5145 in response to the input operation, thereby controlling the position and posture of the endoscope 5115. After the endoscope 5115 at the distal end of the arm portion 5145 has been moved from an arbitrary position to a different arbitrary position by this control, the endoscope 5115 can be supported fixedly at the position after the movement. Note that the arm portion 5145 may be operated by a so-called master-slave system. In this case, the arm portion 5145 may be remotely controlled by the user through the input apparatus 5161 that is installed at a place remote from the operating room.

Further, in the case where force control is applied, the arm control apparatus 5159 may perform so-called power-assisted control to drive the actuators of the joint portions 5147a to 5147c such that the arm portion 5145 may receive external force by the user and move smoothly following the external force. This makes it possible to move the arm portion 5145 with relatively weak force when the user directly touches the arm portion 5145 to move the arm portion 5145. As a result, the user can move the endoscope 5115 more intuitively by a simpler and easier operation, and the convenience to the user can be improved.

Here, in endoscopic surgery, the endoscope 5115 is generally supported by a medical doctor called "scopist." In contrast to this, in the case where the support arm apparatus 5141 is used, the position of the endoscope 5115 can be fixed with a higher degree of certainty without hands, and therefore, an image of a surgical region can be obtained stably and surgery can be performed smoothly.

Note that the arm control apparatus 5159 may not necessarily be provided on the cart 5151. Further, the arm control apparatus 5159 may not necessarily be a single apparatus. For example, the arm control apparatus 5159 may be provided in each of the joint portions 5147a to 5147c of the arm portion 5145 of the support arm apparatus 5141, and the plurality of arm control apparatus 5159 cooperate with each other to control the drive of the arm portion 5145.

(Light Source Apparatus)

The light source apparatus 5157 supplies irradiation light for image capturing of a surgical region to the endoscope 5115. The light source apparatus 5157 includes a white light source that includes, for example, an LED, a laser light source, or a combination of them. Here, in a case where the white light source includes a combination of RGB laser light sources, since the output intensity and the output timing can be controlled with a high degree of accuracy for each color (each wavelength), the white balance of a taken image can be adjusted by the light source apparatus 5157. Further, in this case, when laser beams from the RGB laser light sources are time-divisionally emitted to an object to be observed and the drive of the imaging element of the camera head 5119 is controlled in synchronism with the irradiation timings, images corresponding to the respective R, G and B colors can be taken time-divisionally. According to this method, a color image can be obtained even if a color filter is not provided for the imaging element.

Further, the drive of the light source apparatus 5157 may be controlled such that the intensity of light to be output is changed for each predetermined time. By controlling the drive of the imaging element of the camera head 5119 in synchronism with the timing of the change of the intensity of light to acquire images time-divisionally, and synthesizing the images, an image of a high dynamic range free from so-called blocked up shadows and highlights can be generated.

Further, the light source apparatus 5157 may be configured to supply light of a predetermined wavelength band suitable for special light observation. In special light observation, for example, the wavelength dependency of absorption of light of a body tissue is utilized and light of a band narrower than that of irradiation light for ordinary observation (namely, white light) is emitted, to thereby perform so-called narrow band light observation (Narrow Band Imaging) that captures an image of a predetermined tissue, such as a blood vessel of a superficial portion of the mucous membrane, in a high contrast. Alternatively, in special light observation, fluorescent observation for obtaining an image from fluorescent light that is generated by irradiation of excitation light may also be performed. Fluorescent observation may include, for example, observation of fluorescent light from a body tissue through irradiation of the body tissue with excitation light (autofluorescence observation) or obtainment of a fluorescent light image through local injection of a reagent such as indocyanine green (ICG) into a body tissue and irradiation of the body tissue with excitation light corresponding to the fluorescent light wavelength of the reagent. The light source apparatus 5157 may be configured to supply such narrow-band light and/or excitation light suitable for special light observation as described above.

3. FIRST EMBODIMENT

3.1. System Configuration

Figure 2:
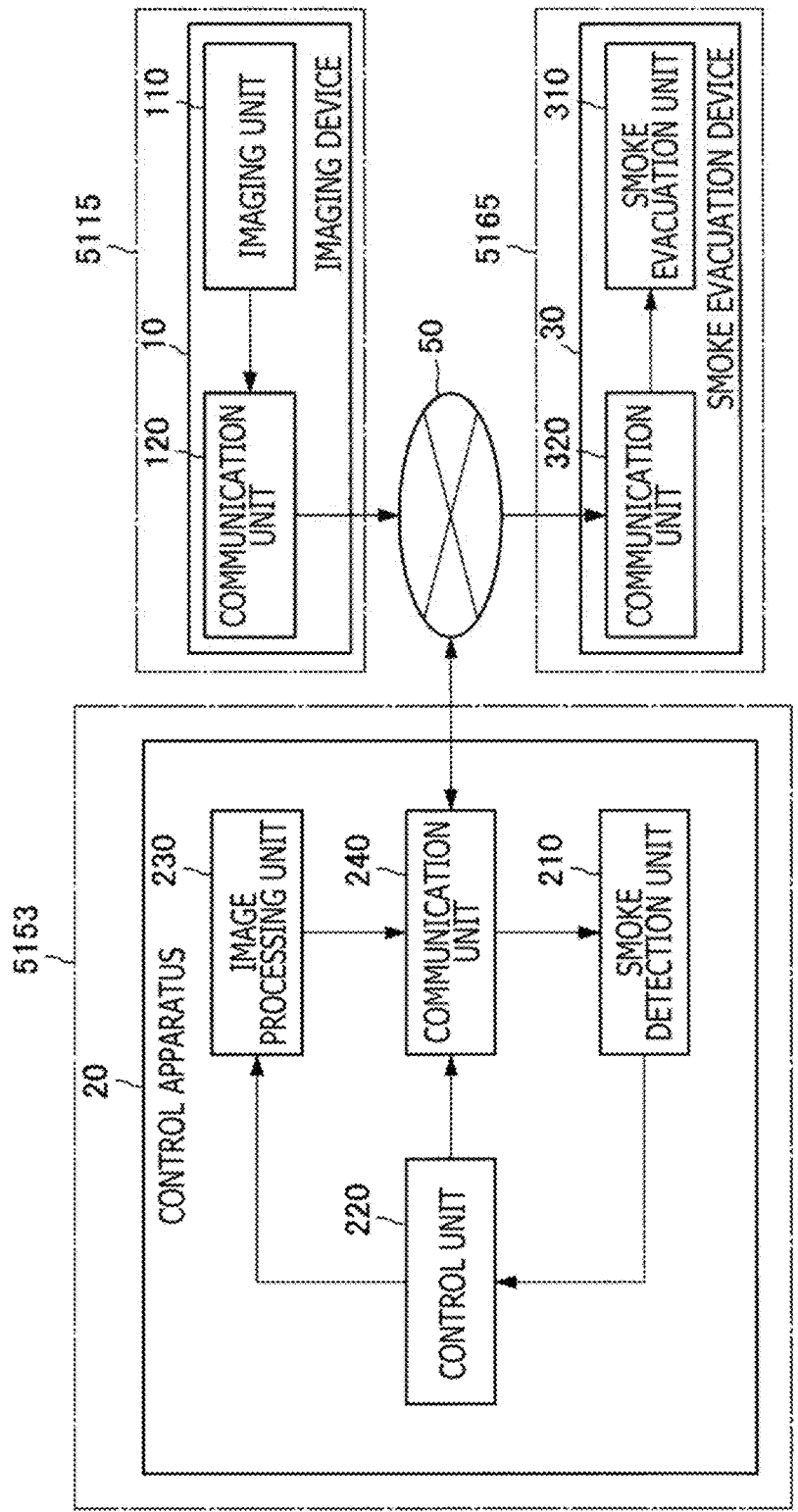
FIG. 2

Next, a first embodiment of the present disclosure is described in detail. An example of a system configuration according to the first embodiment is first described. FIG. 2 is a diagram illustrating an example of the system configuration according to the first embodiment of the present disclosure.

With reference to FIG. 2, a control system according to the present embodiment includes an imaging device 10, a control apparatus 20, and a smoke evacuation device 30. Further, the imaging device 10 and the control apparatus 20, and the control apparatus 20 and the smoke evacuation device 30 are connected to each other via a network 50.

(Imaging Device 10)

The imaging device 10 according to the present embodiment is an apparatus configured to take an image of a living body inside an object to be observed. The imaging device 10 according to the present embodiment may be, for example, the endoscope 5115 illustrated in FIG. 1. Further, the imaging device 10 according to the present embodiment includes, as illustrated in FIG. 2, an imaging unit 110 and a communication unit 120.

((Imaging Unit 110))

The imaging unit 110 functions to take an image of a living body inside an object to be observed. Thus, the imaging unit 110 according to the present embodiment includes an imaging element, for example, a CCD (Charge Coupled Device) or a CMOS (complementary MOS). Here, the image of the living body according to the present embodiment widely includes images that are acquired biologically (Biological Imaging) for a clinical, medical, or experimental purpose, and the objected to be imaged is not limited to human.

((Communication Unit 120))

The communication unit 120 functions to communicate information to/from the control apparatus 20 via the network 50. Specifically, the communication unit 120 transmits an image of a living body taken by the imaging unit 110 to the control apparatus 20.

(Control Apparatus 20)

The control apparatus 20 according to the present embodiment is an information processing apparatus configured to control, on the basis of detected smoke in a living body, the smoke removal processing on an image of the living body and smoke evacuation of evacuating smoke in the living body to outside the body cavity. The control apparatus 20 according to the present embodiment may be, for example, the CCU 5153 illustrated in FIG. 1. Further, the control apparatus 20 according to the present embodiment includes, as illustrated in FIG. 2, a smoke detection unit 210, a control unit 220, an image processing unit 230, and a communication unit 240.

((Smoke Detection Unit 210))

The smoke detection unit 210 functions to detect smoke in a living body. The smoke detection unit 210 according to the present embodiment can detect whether smoke is present in a living body or not, and can calculate, in a case where smoke is present, the amount of smoke. Here, the smoke detection unit 210 according to the present embodiment may perform smoke detection or smoke amount calculation on the basis of, for example, an image of a living body taken by the imaging device 10. More specifically, the smoke detection unit 210 can perform the smoke detection and the smoke amount calculation on the basis of the saturation of an image of a living body.

Figure 3:
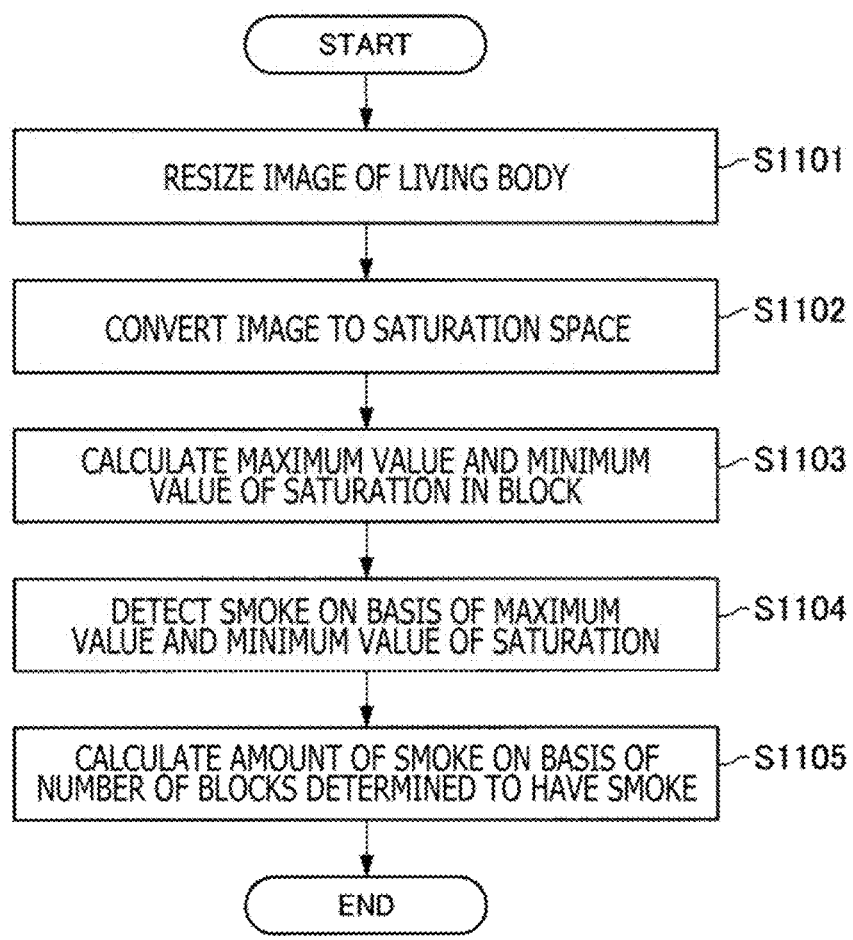
FIG. 3

FIG. 3 is a flow chart illustrating a flow of the smoke detection and smoke amount calculation by the smoke detection unit 210 according to the present embodiment. With reference to FIG. 3, the smoke detection unit 210 according to the present embodiment first performs resize processing on an image of a living body taken by the imaging device 10 (S1101). Here, the smoke detection unit 210 may convert the image of the living body into an image that is $\frac{1}{16}$ times as large as the original one, for example. The above-mentioned processing by the smoke detection unit 210 makes it possible to effectively reduce processing load in the subsequent image processing.

Next, the smoke detection unit 210 converts the image of the living body resized in Step S1101 from an RGB space to a saturation section (S1102). In a case where smoke is present in the living body, the saturation of a taken image of the living body is predicted to be low, and hence the smoke detection unit 210 performs the above-mentioned processing, thereby being capable of efficiently detecting smoke.

Next, the smoke detection unit 210 calculates the maximum value and minimum value of saturation in set blocks of the image of the living body converted to the saturation space in Step S1101 (S1103).

Subsequently, the smoke detection unit 210 determines whether or not smoke is present on the basis of the maximum value and minimum value of saturation calculated in Step S1103 (S1104). Here, a change in saturation due to the effect of smoke is predicted to be settled in a predetermined value range, and hence the smoke detection unit 210 may determine that smoke is present in a case where the maximum value and minimum value of saturation are in a threshold range.

Next, the smoke detection unit 210 calculates an amount of smoke on the basis of the number of blocks determined to have smoke in Step S1104 (S1105). The smoke detection unit 210 may calculate the amount of smoke by multiplying the number of blocks described above and a coefficient set in advance together, for example. That is, the smoke detection unit 210 can calculate the amount of smoke on the basis of a region of the image of the living body in which smoke has been detected.

The flow of the smoke detection and smoke amount calculation by the smoke detection unit 210 according to the present embodiment is described above. Note that, in the case of the example described above with reference to FIG. 3, the smoke detection unit 210 performs the smoke detection and the smoke amount calculation on the basis of the saturation of an image of a living body, but the processing by the smoke detection unit 210 according to the present embodiment is not limited to the example. The smoke detection unit 210 according to the present embodiment may perform the smoke detection or the smoke amount calculation on the basis of a cauterization processing signal from the energy treatment tool 5135, for example. Further, the smoke detection unit 210 can perform the smoke detection or the smoke amount calculation on the basis of sensor information collected by various smoke sensors, for example.

((Control Unit 220))

The control unit 220 functions to control the smoke removal processing on an image of a living body taken by the imaging device 10 and the actual smoke evacuation of smoke in the living body. Here, the smoke removal processing described above means processing of performing the image processing on an image of a living body, thereby removing smoke appearing in the image. Further, the actual smoke evacuation described above means processing of discharging smoke generated in the living body to outside the body cavity.

Here, the control unit 220 according to the present embodiment may execute at least the smoke removal processing described above on the basis of a fact that the smoke detection unit 210 has detected smoke. Further, the control unit 220 may execute the actual smoke evacuation described above in a case where the amount of smoke calculated by the smoke detection unit 210 is a predetermined threshold or more. Here, the control unit 220 can control the level of the actual smoke evacuation on the basis of the amount of smoke calculated.

Figure 4:
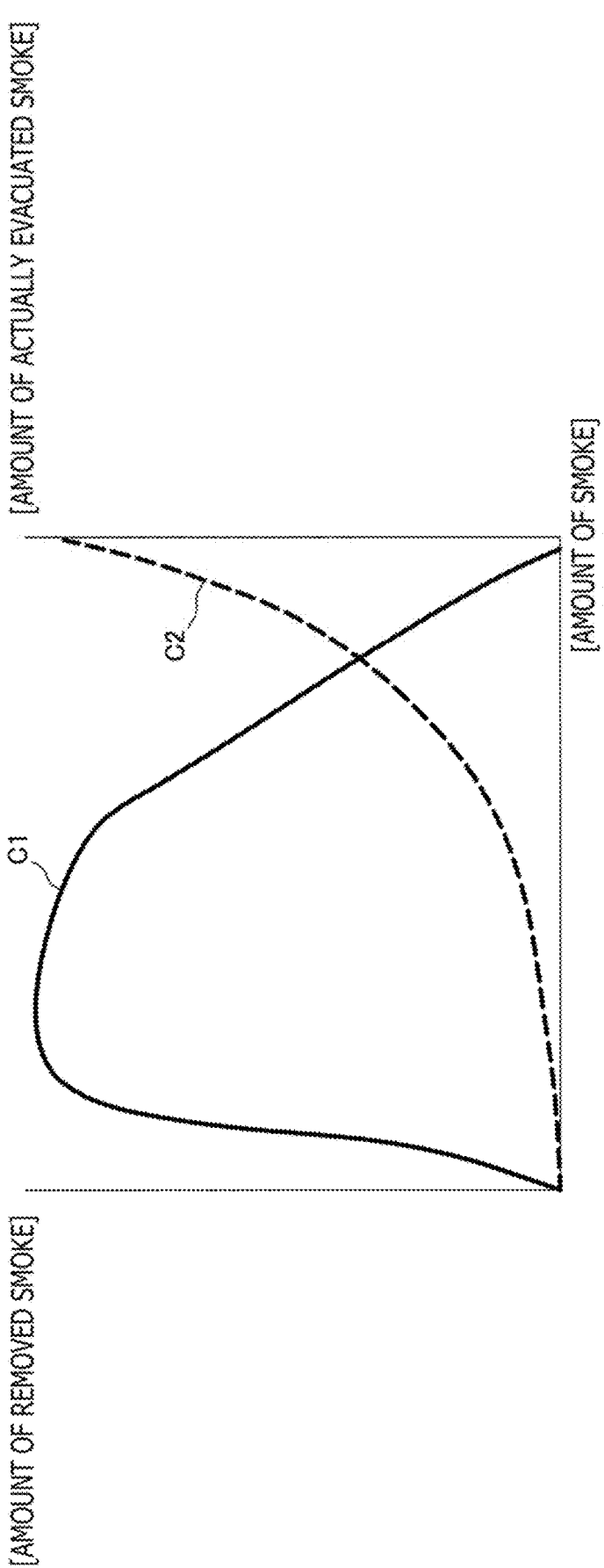
FIG. 4

FIG. 4 is a diagram illustrating a relationship between the smoke removal processing and the actual smoke evacuation, which are controlled by the control unit 220 according to the present embodiment, and the amount of smoke. In FIG. 4, the horizontal axis indicates the amount of smoke and the vertical axis indicates the amount of smoke removed through processing and the amount of actually evacuated smoke. Further, in FIG. 4, the curve C1 indicates the amount of smoke removed through processing and the curve C2 indicates the level of the actual smoke evacuation that is controlled by the control unit 220.

Here, when an attention is paid to the relationship between the curves C1 and C2, it is found that as the amount of smoke is increased, the amount of actually evacuated smoke is increased while the amount of smoke removed through processing is reduced. This is because in a case where the amount of smoke is large, it is difficult to acquire background information of an image of a living body, resulting in a deterioration in smoke removal effect by the image processing. Accordingly, in the case where the amount of smoke is large, the control unit 220 according to the present embodiment increases the level of the actual smoke evacuation, thereby being capable of effectively eliminating the effect of smoke.

((Image Processing Unit 230))

The image processing unit 230 functions to execute the smoke removal processing on an image of a living body on the basis of control by the control unit 220. Here, the image processing unit 230 according to the present embodiment may perform the smoke removal processing described above with the use of a technology widely used in the image processing field, such as dehazing. Meanwhile, a method for the smoke removal processing by the image processing unit 230 is not limited to the above-mentioned example, and various technologies may be used.

((Communication Unit 240))

The communication unit 240 functions to communicate information to/from the imaging device 10 or the smoke evacuation device 30 via the network 50. Specifically, the communication unit 240 receives an image of a living body from the imaging device 10. Further, the communication unit 240 transmits a control signal generated by the control unit 220 to the smoke evacuation device 30.

(Smoke Evacuation Device 30)

The smoke evacuation device 30 according to the present embodiment is an apparatus that functions to execute the actual smoke evacuation on the basis of control by the control apparatus 20. The smoke evacuation device 30 according to the present embodiment may be, for example, the smoke evacuation apparatus 5165 illustrated in FIG. 1. Further, the smoke evacuation device 30 according to the present embodiment includes, as illustrated in FIG. 2, a smoke evacuation unit 310 and a communication unit 320.

((Smoke Evacuation Unit 310))

The smoke evacuation unit 310 functions to execute the actual smoke evacuation of smoke in a living body on the basis of control by the control apparatus 20. Here, the smoke evacuation unit 310 according to the present embodiment can set the level of the actual smoke evacuation on the basis of a received control signal. Note that examples of the smoke evacuation mechanism of the smoke evacuation unit 310 according to the present embodiment include a mechanism for adjusting the amount of smoke to be evacuated through a smoke evacuation tube and a mechanism for controlling the opening/closing portion of a trocar.

((Communication Unit 320))

The communication unit 320 functions to communicate information to/from the control apparatus 20 via the network 50. Specifically, the communication unit 320 receives a control signal related to the actual smoke evacuation of smoke in a living body from the control apparatus 20.

3.2. Flow of Operation of Control Apparatus 20

Figure 5:
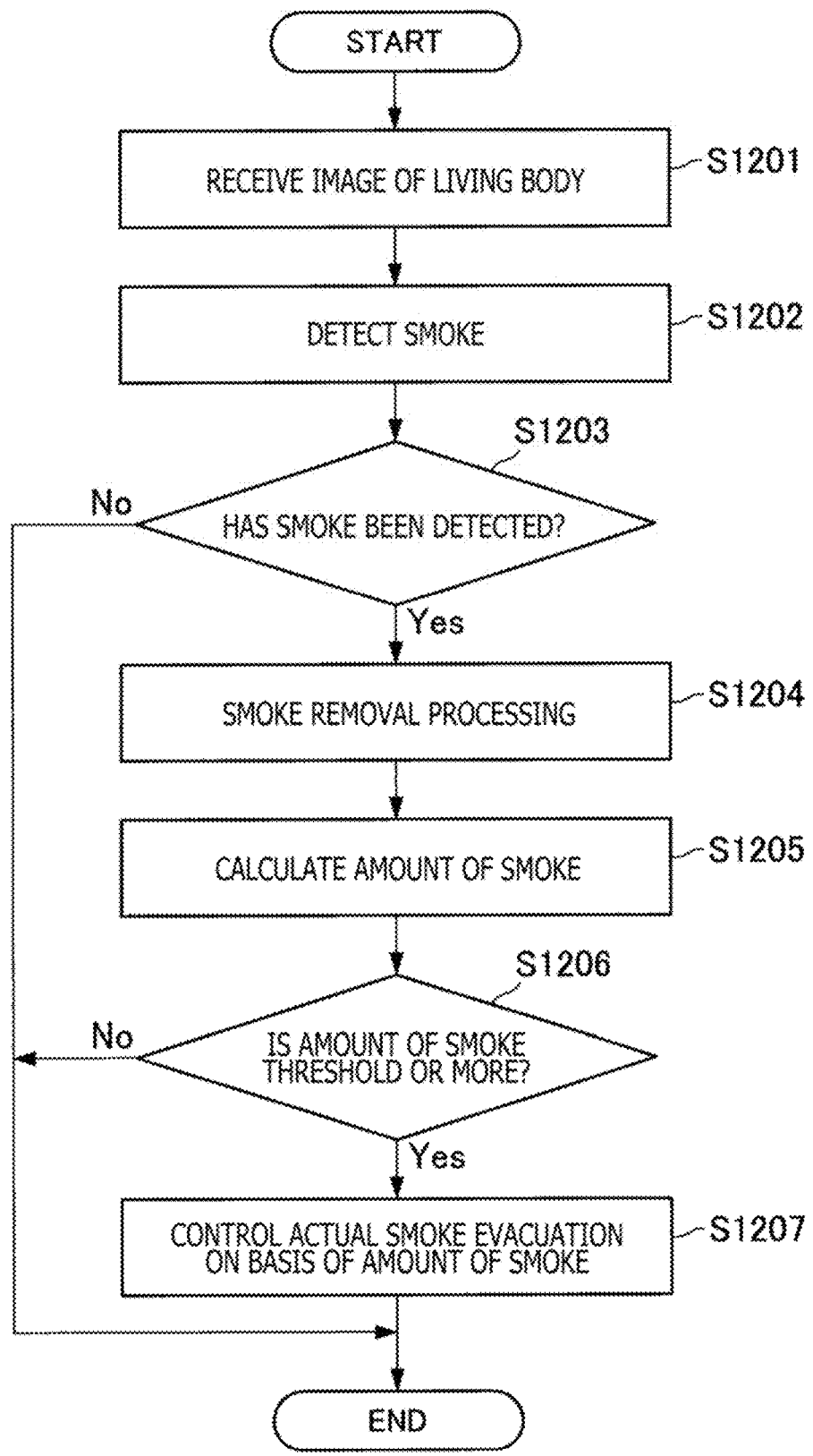
FIG. 5

Next, the flow of operation of the control apparatus 20 according to the present embodiment is described in detail. FIG. 5 is a flow chart illustrating a flow of basic operation of the control apparatus 20 according to the present embodiment.

With reference to FIG. 5, the communication unit 240 first receives an image of a living body from the imaging device 10 (S1201).

Next, the smoke detection unit 210 detects smoke on the basis of the image of the living body received in Step S1201 (S1202). Here, the smoke detection unit 210 according to the present embodiment may detect smoke by performing the processing in Steps S1101 to S1104 illustrated in FIG. 3.

Further, as described above, the smoke detection unit 210 according to the present embodiment can also detect smoke on the basis of a cauterization processing signal from the energy treatment tool S135, for example.

Next, the control unit 220 determines whether or not smoke has been detected in Step S1202 (S1203). In a case where no smoke has been detected (S1203: No), the control apparatus 20 may transition to a standby state.

In a case where smoke has been detected (S1203: Yes), on the other hand, the control unit 220 controls the image processing unit 230 to perform the smoke removal processing on the image of the living body (S1204).

Further, the smoke detection unit 210 subsequently calculates the amount of smoke (S1205). Here, the smoke detection unit 210 may calculate the amount of smoke by performing the processing in Step S1105 illustrated in FIG. 3.

Next, the control unit 220 determines whether or not the amount of smoke calculated in Step S1205 is a threshold or more (S1206). In a case where the amount of smoke is less than the threshold (S1206: No), the control apparatus 20 transitions to the standby state.

In a case where the amount of smoke is the threshold or more (S1206: Yes), on the other hand, the control unit 220 controls the actual smoke evacuation of smoke on the basis of the amount of smoke calculated in Step S1205 (S1207). Specifically, the control unit 220 can control the smoke evacuation device 30 to execute the actual smoke evacuation at a level suitable for the amount of smoke calculated.

The flow of basic operation of the control apparatus 20 according to the present embodiment is described in detail above. In this way, according to the control apparatus 20 of the present embodiment, the processing for smoke effect elimination can be automatically controlled, which allows the surgeon to focus on surgical operation. Thus, according to the control apparatus 20 of the present embodiment, through the smoke removal processing and the actual smoke evacuation, not only a surgical field is ensured with a higher degree of certainty, but also effects such as a reduction in surgery time are expected.

Note that, in the case of the example described above with reference to FIG. 5, the control apparatus 20 according to the present embodiment performs the smoke detection only once and controls, in a case where smoke has been detected in the smoke detection, the smoke removal processing and the actual smoke evacuation. Meanwhile, the control apparatus 20 according to the present embodiment can perform the smoke detection again after executing the smoke removal processing and control the actual smoke evacuation on the basis of a fact that smoke has been detected in the second smoke detection. In this case, the effect of smoke that has remained after the smoke removal processing can be eliminated by the actual smoke evacuation, and the amount of smoke to be actually evacuated can be minimized, with the result that effects on an object to be observed, which are due to pneumoperitoneum gas cost or hemodynamic changes, can be reduced.

Figure 6:
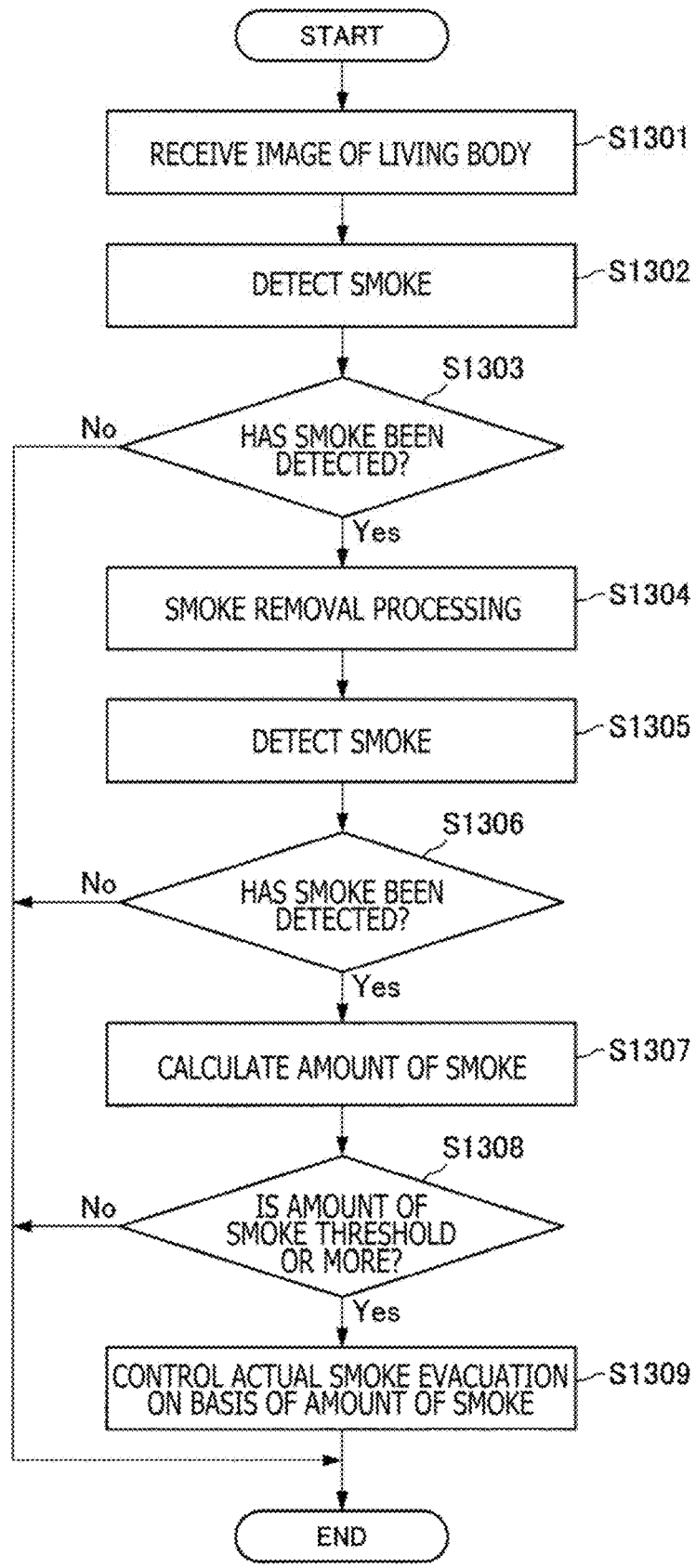
FIG. 6

FIG. 6 is a flow chart illustrating a flow of actual smoke evacuation control based on smoke detection after the smoke removal processing by the control apparatus 20 according to the present embodiment.

With reference to FIG. 6, as in the case illustrated in FIG. 5, the communication unit 240 first receives an image of a living body from the imaging device 10 (S1301).

Next, the smoke detection unit 210 performs the first smoke detection on the basis of the image of the living body received in Step S1301 (S1302).

Next, the control unit 220 determines whether or not smoke has been detected in Step S1302 (S1303). In a case where no smoke has been detected (S1303: No), the control apparatus 20 transitions to the standby state.

In a case where smoke has been detected (S1303: Yes), on the other hand, the control unit 220 controls the image processing unit 230 to execute the smoke removal processing on the image of the living body (S1304).

Further, the smoke detection unit 210 subsequently performs the second smoke detection on the basis of the image of the living body subjected to the smoke removal processing in Step S1304 (S1305).

Next, the control unit 220 determines whether or not smoke has been detected in the second smoke detection in Step S1305 (S1306). In a case where no smoke has been detected (S1306: No), the control apparatus 20 may transition to the standby state.

In a case where smoke has been detected (S1306: Yes), on the other hand, the smoke detection unit 210 calculates the amount of smoke (S1307).

Next, the control unit 220 determines whether or not the amount of smoke calculated in Step S1307 is a threshold or more (S1308). In a case where the amount of smoke is less than the threshold (S1308: No), the control apparatus 20 transitions to the standby state.

In a case where the amount of smoke is the threshold or more (S1308: Yes), on the other hand, the control unit 220 controls the actual smoke evacuation of smoke on the basis of the amount of smoke calculated in Step S1205 (S1309).

The flow of the actual smoke evacuation control based on the smoke detection after the smoke removal processing by the control apparatus 20 according to the present embodiment is described above. In this way, the frequency of the smoke detection, smoke amount calculation, smoke removal processing, or actual smoke evacuation by the control apparatus 20 according to the present embodiment is flexibly changeable. This means that the processing processes by the control apparatus 20 according to the present embodiment are not necessarily executed in the order illustrated in the flow charts of FIG. 5 and FIG. 6. The processing by the control apparatus 20 according to the present embodiment may be appropriately designed depending on the specifications of each configuration or the specifications of surgery, for example.

4. SECOND EMBODIMENT

4.1. System Configuration Example

Next, a second embodiment of the present disclosure is described. In the case of the above-mentioned first embodiment, the control apparatus 20 according to the first embodiment is the CCU 5153 and controls the smoke removal processing on an image of a living body taken by the imaging device 10 or the actual smoke evacuation by the smoke evacuation device 30.

Meanwhile, the imaging function, smoke detection function, control function, image processing function, and smoke evacuation function according to the present technical ideas are not limited to the examples described above, and may be implemented as one of functions of various apparatus. A control apparatus 20 according to the second embodiment of the present disclosure may be, for example, the endoscope 5115 illustrated in FIG. 1.

Figure 7:
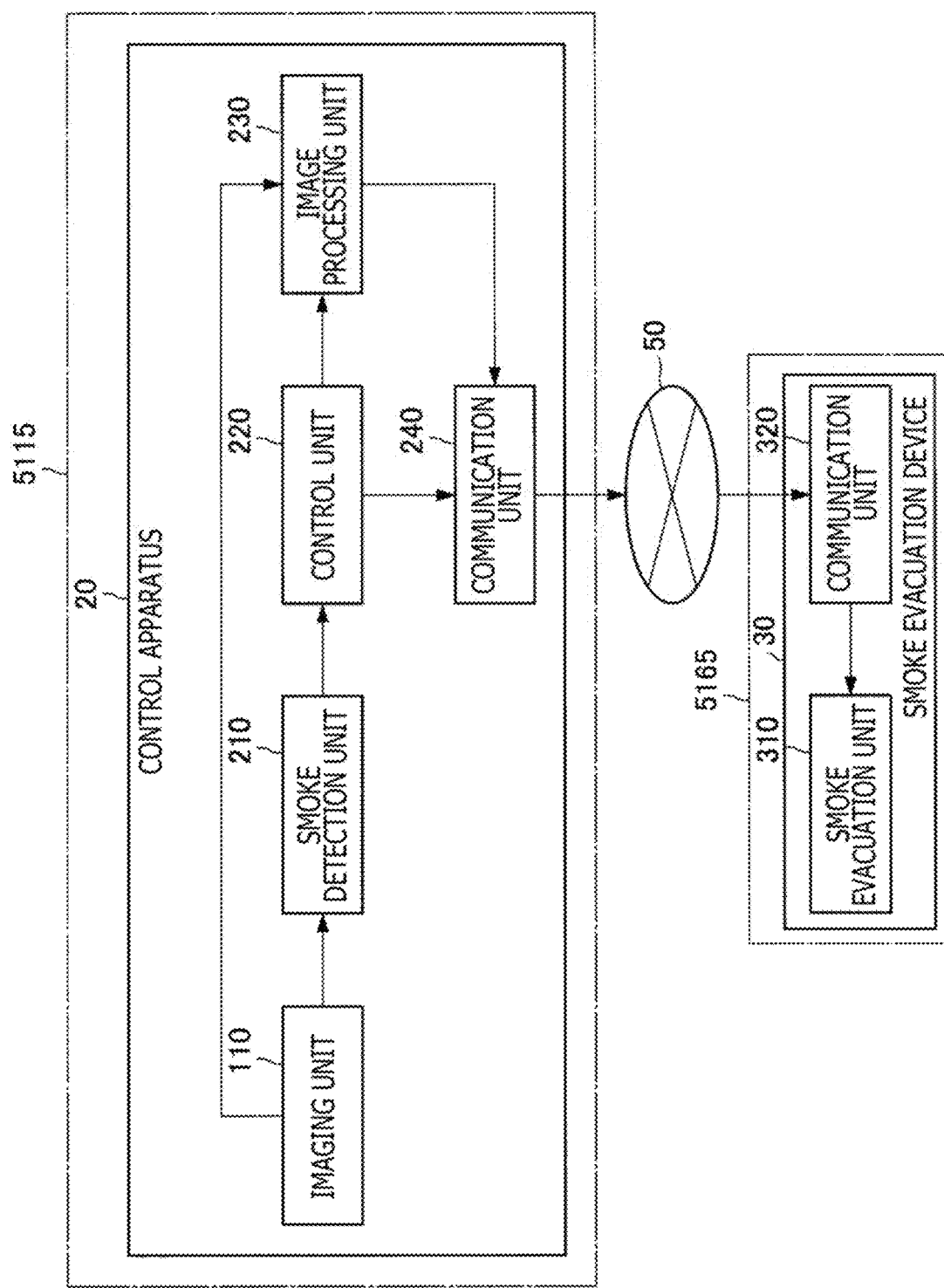
FIG. 7

FIG. 7 is a diagram illustrating an example of a system configuration according to the second embodiment of the present disclosure. As described above, the control apparatus 20 according to the present embodiment is implemented as the endoscope 5115. Here, the control apparatus 20 according to the present embodiment may further include the imaging unit 110 in addition to the components of the control apparatus 20 according to the first embodiment.

That is, the control apparatus 20 according to the present embodiment may have the imaging function, the smoke detection function, the control function, and the image processing function. The control apparatus 20 according to the present embodiment can control, on the basis of the amount of smoke calculated, the smoke evacuation device 30 to execute the actual smoke evacuation.

Note that the function of each configuration and flow of operation of the control apparatus 20 according to the present embodiment are substantially the same as those of the first embodiment, and the detailed description thereof is thus omitted.

5. THIRD EMBODIMENT

5.1. System Configuration Example

Next, a third embodiment of the present disclosure is described. In the cases of the above-mentioned first embodiment and second embodiment, the control apparatus 20 is the CCU 5153 or the endoscope 5115. Meanwhile, a control apparatus 20 according to the third embodiment of the present disclosure may be the smoke evacuation apparatus 5165 illustrated in FIG. 1.

Figure 8:
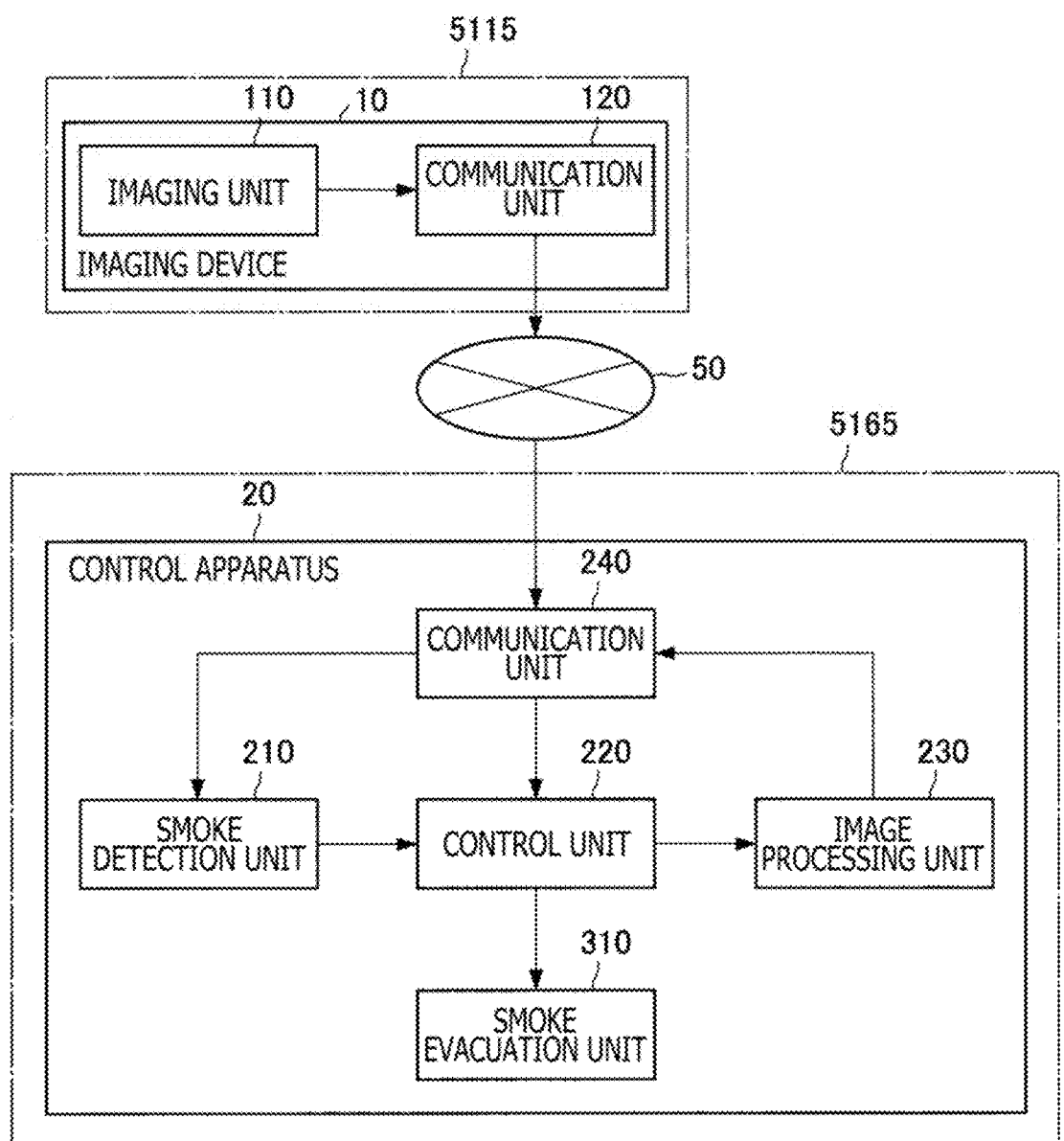
FIG. 8

FIG. 8 is a diagram illustrating an example of a system configuration according to the third embodiment of the present disclosure. As described above, the control apparatus 20 according to the present embodiment is implemented as the smoke evacuation apparatus 5165. Here, the control apparatus 20 according to the present embodiment may further include the smoke evacuation unit 310 in addition to the components of the control apparatus 20 according to the first embodiment.

That is, the control apparatus 20 according to the present embodiment may have the smoke detection function, the control function, the image processing function, and the smoke evacuation function. The control apparatus 20 according to the present embodiment can receive an image of a living body taken by the imaging device 10 and execute the smoke detection, the smoke amount calculation, the smoke removal processing, and the actual smoke evacuation.

Note that the function of each configuration and flow of operation of the control apparatus 20 according to the present embodiment are substantially the same as those of the first embodiment, and the detailed description thereof is thus omitted.

6. FOURTH EMBODIMENT

6.1. System Configuration Example

Next, a fourth embodiment of the present disclosure is described. In the cases of the above-mentioned first embodiment to third embodiment, the control apparatus 20 is the CCU 5153, the endoscope 5115, or the smoke evacuation apparatus 5165. Meanwhile, a control apparatus 20 according to the fourth embodiment of the present disclosure may be an operating room control apparatus. Here, the operating room control apparatus according to the present embodiment is an apparatus configured to control the operations of medical equipment and non-medical equipment of the operating room system 5100 illustrated in FIG. 1 in a cooperated manner. An operating room control apparatus 5109 according to the present embodiment is first described.

The operating room control apparatus 5109 controls processing other than image display processing of the non-medical equipment in a centralized manner. The operating room control apparatus 5109 controls the drive of the patient bed 5183, the ceiling camera 5187, the operating theater camera 5189, and the lighting 5191, for example.

The operating room system 5100 includes the centralized operation panel 5111, and the user can issue, through the centralized operation panel 5111, an instruction related to image display to the audiovisual controller 5107 or an instruction related to the operation of the non-medical equipment to the operating room control apparatus 5109. The centralized operation panel 5111 includes a touch panel on the display surface of the display apparatus.

Figure 9:
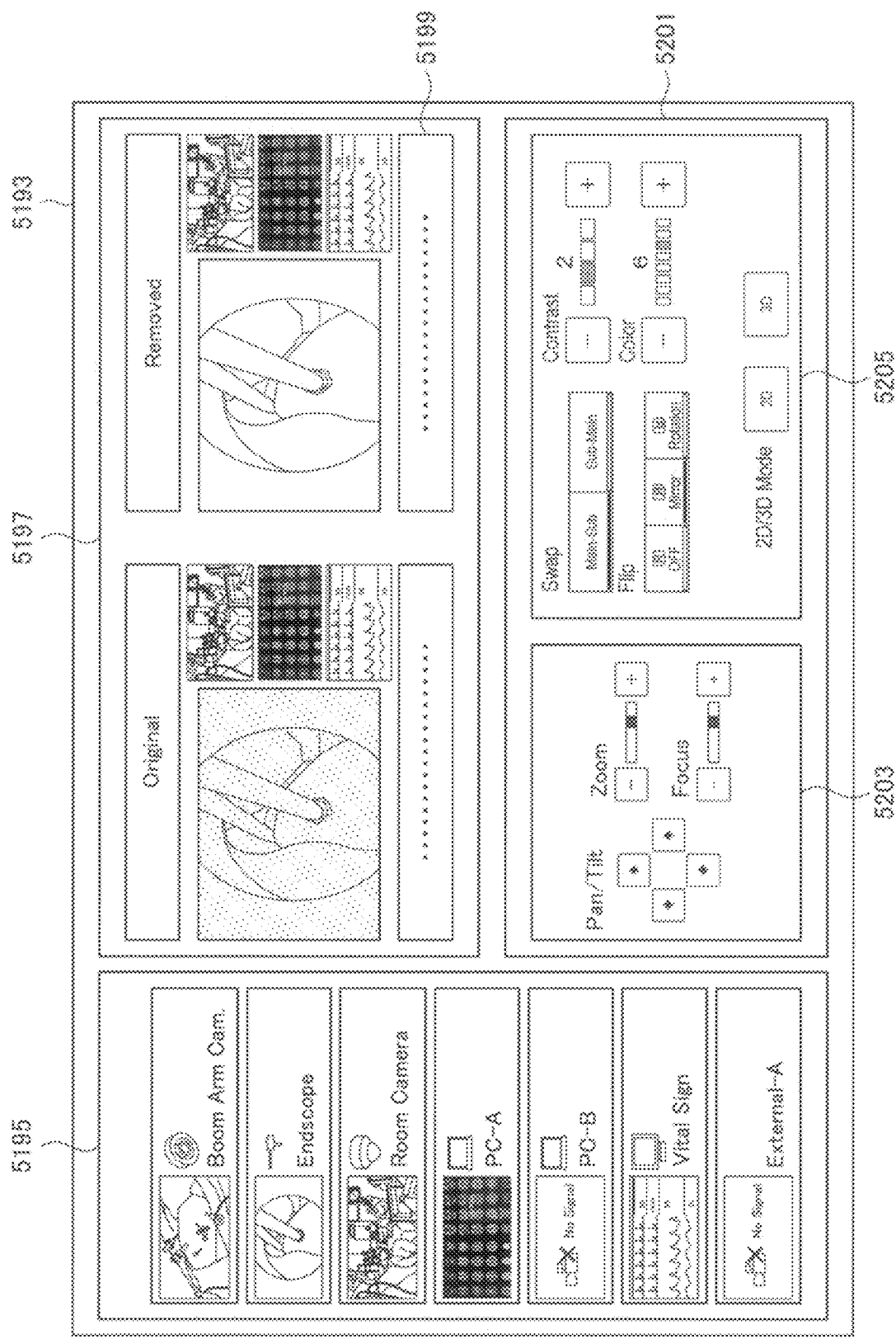
FIG. 9

FIG. 9 is a diagram illustrating a display example of the operation screen of the centralized operation panel 5111. FIG. 9 illustrates, as an example, an operation screen corresponding to a case where the operating room system 5100 includes two display apparatus as output destination apparatus. With reference to FIG. 9, an operation screen 5193 includes a sending source selection region 5195, a preview region 5197, and a control region 5201.

In the sending source selection region 5195, sending source apparatus provided in the operating room system 5100 and thumbnail screens representing display information that the sending source apparatus have are displayed in association with each other. The user can select, as an apparatus having display information to be displayed on the display apparatus, any of the sending source apparatus displayed in the sending source selection region 5195.

In the preview region 5197, previews of screens that are displayed on the display apparatus, which are output destination apparatus, are displayed. In the example illustrated in FIG. 9, taken original images of a living body and images of the living body subjected to the smoke removal processing are displayed. Further, in the example illustrated in FIG. 9, four images are displayed in the left and right display regions by PinP. The four images correspond to display information sent from a sending source apparatus selected in the sending source selection region 5195. One of the four images is displayed in a relatively large size as a main image while the remaining three images are displayed in a relatively small size as sub images. The user can exchange the main image and the sub images by appropriately selecting one of the four images displayed in the region. Further, a status display region 5199 is provided below the region in which the four images are displayed, and a status related to surgery (for example, elapsed time of surgery or physical information of patient) may be appropriately displayed in the status display region 5199.

The control region 5201 includes a sending source operation region 5203 and an output destination operation region 5205. In the sending source operation region 5203, a GUI (Graphical User Interface) part for performing operation for a sending source apparatus is displayed. In the output destination operation region 5205, a GUI part for performing operation for an output destination apparatus is displayed. In the example illustrated in FIG. 9, GUI parts for performing various operations for a camera (panning, tilting, and zooming) in a sending source apparatus having the imaging function are provided in the sending source operation region 5203. The user can control the operation of the camera of the sending source apparatus by appropriately selecting any of these GUI parts. Note that, although not illustrated, in a case where the sending source apparatus selected in the sending source selection region 5195 is a recorder (that is, a case where an image recorded on the recorder in the past is displayed in the preview region 5197), GUI parts for performing such operations as reproduction of the image, stopping of reproduction, rewinding, fast-feeding, and so forth may be provided in the sending source operation region 5203.

Further, in the output destination operation region 5205, GUI parts for performing various operations for display on a display apparatus that is an output destination apparatus (swap, flip, color adjustment, contrast adjustment, and switching between 2D display and 3D display) are provided. The user can operate the display of the display apparatus by appropriately selecting any of these GUI parts.

Note that the operation screen to be displayed on the centralized operation panel 5111 is not limited to the example illustrated in FIG. 9, and the user may be able to perform, through the centralized operation panel 5111, input operation to each apparatus that may be controlled by the audiovisual controller 5107 and the operating room control apparatus 5109, which are provided in the operating room system 5100.

The operating room control apparatus 5109 according to the present embodiment and the present embodiment is described above. Subsequently, an example of a system configuration according to the present embodiment is described.

Figure 10:
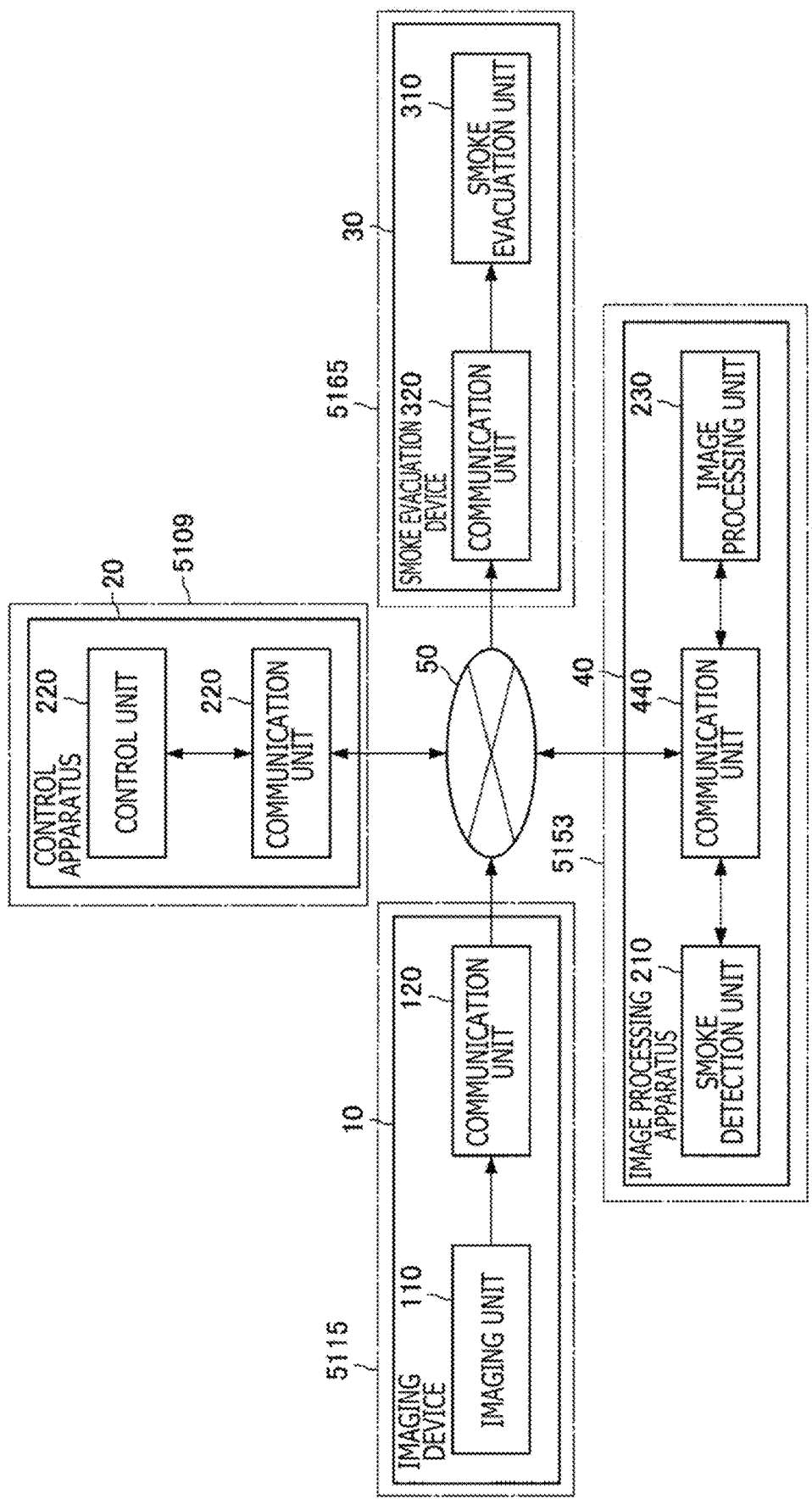
FIG. 10

FIG. 10 is a diagram illustrating an example of the system configuration according to the fourth embodiment of the present disclosure. As described above, the control apparatus 20 according to the present embodiment is implemented as the operating room control apparatus 5109. Here, the control apparatus 20 according to the present embodiment may include the control unit 220 and the communication unit 240.

That is, the control apparatus 20 according to the present embodiment has the control function. Here, the control apparatus 20 according to the present embodiment may control the smoke detection unit 210 and the image processing unit 230 of the image processing apparatus 40, which is implemented as the CCU 5153, and the smoke evacuation unit 310 of the smoke evacuation device 30 in a centralized manner. Specifically, the control apparatus 20 according to the present embodiment may control, on the basis of a fact that the image processing apparatus 40 has detected smoke, the image processing apparatus 40 to execute the smoke removal processing. Further, the control apparatus 20 can control, on the basis of the amount of smoke calculated by the image processing apparatus 40, the smoke evacuation device 30 to perform the actual smoke evacuation.

Note that the function of each configuration and flows of operations of the control apparatus 20 and the image processing apparatus 40 according to the present embodiment are substantially the same as those of the first embodiment, and the detailed description thereof is thus omitted.

7. HARDWARE CONFIGURATION EXAMPLE

Figure 11:
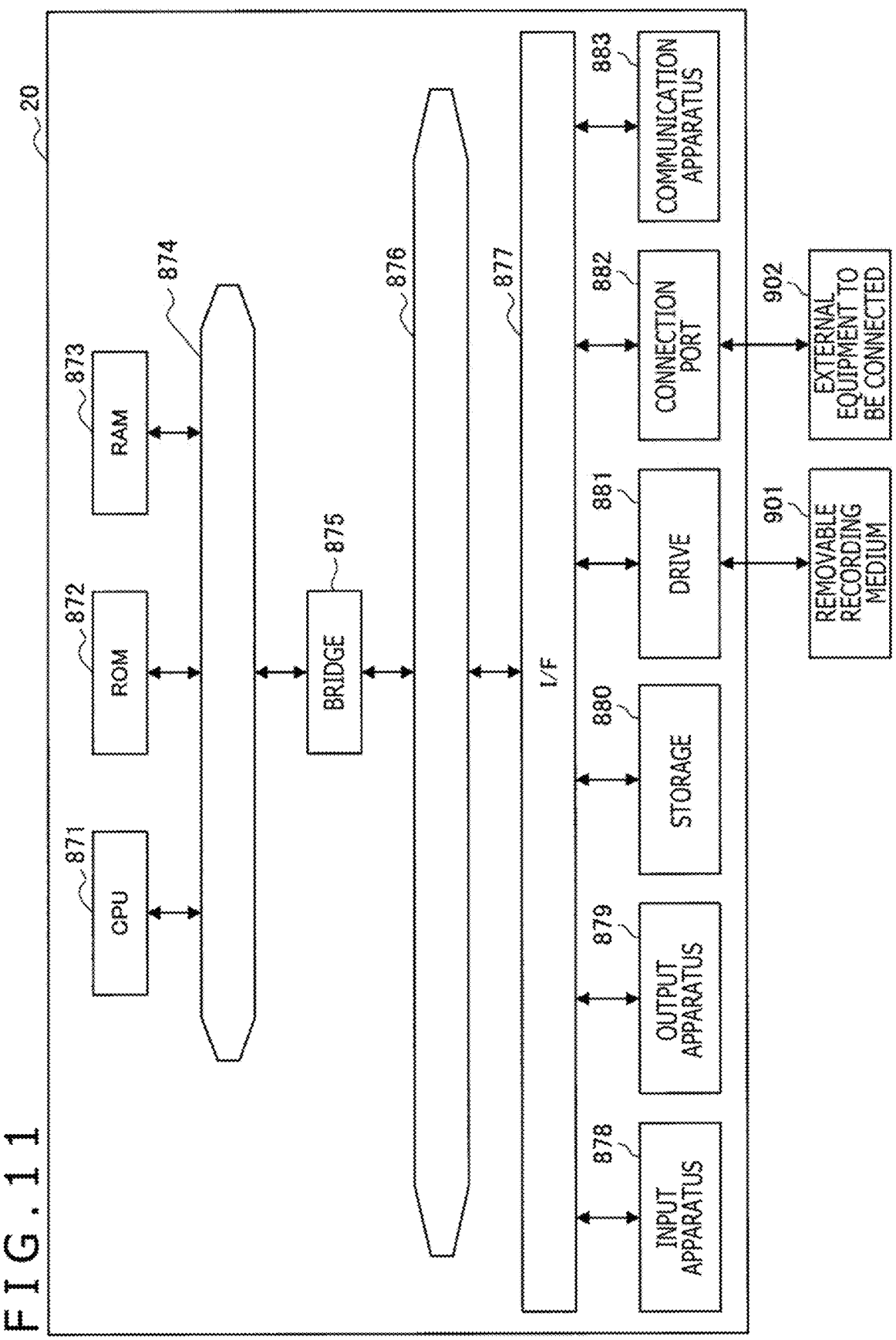
FIG. 11

Next, an example of the hardware configuration of the control apparatus 20 according to one embodiment of the present disclosure is described. FIG. 11 is a block diagram illustrating an example of the hardware configuration of the control apparatus 20 according to one embodiment of the present disclosure. With reference to FIG. 11, the control apparatus 20 includes, for example, a CPU 871, a ROM 872, a RAM 873, a host bus 874, a bridge 875, an external bus 876, an interface 877, an input apparatus 878, an output apparatus 879, a storage 880, a drive 881, a connection port 882, and a communication apparatus 883. Note that the illustrated hardware configuration is an example, and a part of the components may be omitted. Further, the control apparatus 20 may further include components other than the illustrated components.

(CPU 871)

The CPU 871 functions as, for example, an arithmetic processing apparatus or a control apparatus, and controls the entire or part of the operation of each component on the basis of various programs recorded on the ROM 872, the RAM 873, the storage 880, or the removable recording medium 901.

(ROM 872 and RAM 873)

The ROM 872 is means for storing, for example, programs to be read by the CPU 871 or data for calculation. The RAM 873 temporarily or permanently stores, for example, programs to be read by the CPU 871 and various parameters that are changed appropriately in execution of the programs.

(Host Bus 874, Bridge 875, External Bus 876, and Interface 877)

The CPU 871, the ROM 872, and the RAM 873 are connected to each other through the host bus 874 supporting high-speed data transmission, for example. Meanwhile, the host bus 874 is connected to, through the bridge 875, the external bus 876 only supporting relatively low-speed data transmission, for example. Further, the external bus 876 is connected to various components through the interface 877.

(Input Apparatus 878)

Examples of the input apparatus 878 include mice, keyboards, touch panels, buttons, switches, and levers. In addition, as the input apparatus 878, a remote controller capable of transmitting control signals with the use of infrared radiation or other radio waves is sometimes used. Further, the input apparatus 878 includes a voice input apparatus such as a microphone.

(Output Apparatus 879)

The output apparatus 879 is an apparatus capable of notifying a user of acquired information visually or aurally. Examples of the output apparatus 879 include display apparatus including CRT (Cathode Ray Tubes), LCDs, and organic ELs, audio output apparatuses including speakers and headphones, printers, cell phones, and facsimiles.

(Storage 880)

The storage 880 is an apparatus configured to store various pieces of data. Examples of the storage 880 include magnetic storage devices such as hard disk drives (HDD), semiconductor storage devices, optical storage devices, and magneto-optical storage devices.

(Drive 881)

The drive 881 is, for example, an apparatus configured to read out information recorded on the removable recording medium 901, which is a magnetic disk, an optical disc, a magneto-optical disc, or a semiconductor memory, for example, or to write information to the removable recording medium 901.

(Removable Recording Medium 901)

Examples of the removable recording medium 901 include DVD media, Blu-ray (registered trademark) media, HD DVD media, and various semiconductor storage media. As a matter of course, the removable recording medium 901 may be, for example, an IC card having mounted thereon a contactless IC chip or electronic equipment.

(Connection Port 882)

The connection port 882 is a port for connection with an external equipment to be connected 902. Examples of the connection port 882 include USB (Universal Serial Bus) ports, IEEE 1394 ports, SCSI (Small Computer System Interface), RS-232C ports, and optical audio terminals.

(External Equipment to be Connected 902)

Examples of the external equipment to be connected 902 include printers, portable audio players, digital cameras, digital video cameras, and IC recorders.

(Communication Apparatus 883)

The communication apparatus 883 is a communication device for connection with a network. Examples of the communication apparatus 883 include wired or wireless LANs, Bluetooth (registered trademark), communication cards for WUSB (Wireless USB), routers for optical communication, routers for ADSL (Asymmetric Digital Subscriber Line), and modems for various communications.

8. CONCLUSION

As described so far, the control apparatus 20 according to one embodiment of the present disclosure functions to control the smoke removal processing on an image of a living body taken during surgery and the actual smoke evacuation of smoke in the living body. Here, the control apparatus 20 according to one embodiment of the present disclosure can execute at least the smoke removal processing described above on the basis of a fact that smoke has been detected. Further, the control apparatus 20 can control the execution and execution level of the actual smoke evacuation on the basis of the amount of smoke calculated. According to such a configuration, the effect of smoke that is generated by cauterization of a tissue can be more effectively eliminated.

The preferred embodiments of the present disclosure are described in detail so far with reference to the attached drawings, but the technical scope of the present disclosure is not limited to the examples. It is apparent that various changes or modifications could be arrived at by a person who has ordinary knowledge in the technical field to which the present disclosure belongs within the scope of the technical ideas described in the appended claims, and it is therefore understood that such changes or modifications naturally belong to the technical scope of the present disclosure.

Further, the effects described herein are merely illustrative or exemplary and are not limited. That is, the technology according to the present disclosure may provide other effects that are obvious for a person skilled in the art from the description of the present specification, in addition to the above-mentioned effects or instead of the above-mentioned effects.

Note that the following configurations also belong to the technical scope of the present disclosure.

(1)

A control apparatus including:

a control unit configured to control smoke removal processing on an image of a living body taken and actual smoke evacuation of smoke in the living body, in which the control unit allows execution of at least the smoke removal processing on the basis of a fact that the smoke has been detected.

(2)

The control apparatus according to Item (1), in which the control unit controls execution of the actual smoke evacuation on the basis of an amount of smoke calculated.

(3)

The control apparatus according to Item (2), in which the control unit allows execution of the actual smoke evacuation in a case where the amount of smoke is a threshold or more.

(4)

The control apparatus according to Item (2) or (3), in which the control unit controls a level of the actual smoke evacuation on the basis of the amount of smoke.

(5)

The control apparatus according to any one of Items (1) to (4), in which the control unit controls execution of the actual smoke evacuation on the basis of a fact that the smoke has been detected after execution of the smoke removal processing.

(6)

The control apparatus according to any one of Items (1) to (5), in which the smoke is detected on the basis of the image of the living body.

(7)

The control apparatus according to any one of Items (1) to (6), in which the smoke is detected on the basis of saturation of the image of the living body.

(8)

The control apparatus according to any one of Items (1) to (7), in which an amount of smoke is calculated on the basis of a region of the image of the living body in which the smoke has been detected.

(9)

The control apparatus according to any one of Items (1) to (8), further including:

a smoke detection unit configured to detect the smoke.

(10)

The control apparatus according to Item (9), in which the smoke detection unit calculates an amount of smoke.

(11)

The control apparatus according to any one of Items (1) to (10), further including:

an image processing unit configured to execute the smoke removal processing on the image of the living body on the basis of control by the control unit.

(12)

The control apparatus according to any one of Items (1) to (11), further including:

a smoke evacuation unit configured to execute the actual smoke evacuation of the smoke on the basis of control by the control unit.

(13)

The control apparatus according to any one of Items (1) to (12), further including:

an imaging unit configured to take the image of the living body.

(14)

The control apparatus according to any one of Items (1) to (13), in which the control apparatus includes an operating room control apparatus.

(15)

The control apparatus according to any one of Items (1) to (14), in which the image of the living body is an image taken by an endoscope.

(16)

The control apparatus according to any one of Items (1) to (13), in which the control apparatus is a smoke evacuation apparatus.

(17)
A control method including:
controlling, by a processor, smoke removal processing on an image of a living body taken and actual smoke evacuation of smoke in the living body,
in which the controlling includes allowing execution of at least the smoke removal processing on the basis of a fact that the smoke has been detected.
(18)
A control system including:
an endoscope configured to take an image of a living body;
a control apparatus configured to control smoke removal processing on the image of the living body and actual smoke evacuation of smoke in the living body; and
a smoke evacuation apparatus configured to execute the actual smoke evacuation of the smoke on a basis of control by the control apparatus,
in which the control apparatus executes at least the smoke removal processing on the basis of a fact that the smoke has been detected.
(19)
A program for causing a computer to function as a control apparatus,
the control apparatus including a control unit configured to control smoke removal processing on an image of a living body taken and actual smoke evacuation of smoke in the living body,
in which the control unit allows execution of at least the smoke removal processing on the basis of a fact that the smoke has been detected.

REFERENCE SIGNS LIST

10 Imaging device
110 Imaging unit
120 Communication unit
20 Control apparatus
210 Smoke detection unit
220 Control unit
230 Image processing unit
240 Communication unit
30 Smoke evacuation device
310 Smoke evacuation unit
320 Communication unit
40 Image processing apparatus
5109 Operating room control apparatus
5115 Endoscope
5153 CCU
5165 Smoke evacuation apparatus

The invention claimed is:

1. A control apparatus, comprising:
a control unit configured to control smoke removal processing on an image of a living body taken during surgery and actual smoke evacuation of smoke in the living body,
wherein the control unit allows execution of at least the smoke removal processing on a basis of a fact that the smoke has been detected.

2. The control apparatus according to claim 1, wherein the control unit controls execution of the actual smoke evacuation on a basis of an amount of smoke calculated.

3. The control apparatus according to claim 2, wherein the control unit allows execution of the actual smoke evacuation in a case where the amount of smoke is a threshold or more.

4. The control apparatus according to claim 2, wherein the control unit controls a level of the actual smoke evacuation on a basis of the amount of smoke.

5. The control apparatus according to claim 1, wherein the control unit controls execution of the actual smoke evacuation on a basis of a fact that the smoke has been detected after execution of the smoke removal processing.

6. The control apparatus according to claim 1, wherein the smoke is detected on a basis of the image of the living body.

7. The control apparatus according to claim 1, wherein the smoke is detected on a basis of saturation of the image of the living body.

8. The control apparatus according to claim 1, wherein an amount of smoke is calculated on a basis of a region of the image of the living body in which the smoke has been detected.

9. The control apparatus according to claim 1, further comprising:
a smoke detection unit configured to detect the smoke.

10. The control apparatus according to claim 9, wherein the smoke detection unit calculates an amount of smoke.

11. The control apparatus according to claim 1, further comprising:
an image processing unit configured to execute the smoke removal processing on the image of the living body on a basis of control by the control unit.

12. The control apparatus according to claim 1, further comprising:
a smoke evacuation unit configured to execute the actual smoke evacuation of the smoke on a basis of control by the control unit.

13. The control apparatus according to claim 1, further comprising:
an imaging unit configured to take the image of the living body.

14. The control apparatus according to claim 1, wherein the control apparatus includes an operating room control apparatus.

15. The control apparatus according to claim 1, wherein the image of the living body includes an image taken by an endoscope.

16. The control apparatus according to claim 1, wherein the control apparatus includes a smoke evacuation apparatus.

17. A control method, comprising:
controlling, by a processor, smoke removal processing on an image of a living body taken during surgery and actual smoke evacuation of smoke in the living body,
wherein the controlling includes allowing execution of at least the smoke removal processing on a basis of a fact that the smoke has been detected.

18. A control system, comprising:
an endoscope configured to take an image of a living body during surgery;
a control apparatus configured to control smoke removal processing on the image of the living body and actual smoke evacuation of smoke in the living body; and
a smoke evacuation apparatus configured to execute the actual smoke evacuation of the smoke on a basis of control by the control apparatus,
wherein the control apparatus executes at least the smoke removal processing on a basis of a fact that the smoke has been detected.

19. A non-transitory computer-readable medium having stored thereon computer-executable instructions that, when executed by a processor of an information processing apparatus, cause the processor to execute operations, the operations comprising:
   controlling smoke removal processing on an image of a living body taken during surgery and actual smoke evacuation of smoke in the living body,
   wherein the controlling includes allowing execution of at least the smoke removal processing on a basis of a fact that the smoke has been detected.

* * * * *